US008894973B2

(12) United States Patent
Pettegrew et al.

(10) Patent No.: US 8,894,973 B2
(45) Date of Patent: Nov. 25, 2014

(54) METHOD AND SYSTEM FOR DIFFERENTIAL DIAGNOSIS OF CHRONIC SCHIZOPHRENIA AND CHRONIC ALCOHOLISM

(76) Inventors: Jay W. Pettegrew, Cleveland Heights, OH (US); Kanagasabai Panchalingam, Monroeville, PA (US)

( * ) Notice: Subject to any disclaimer, the term of this patent is extended or adjusted under 35 U.S.C. 154(b) by 123 days.

(21) Appl. No.: 13/584,254

(22) Filed: Aug. 13, 2012

(65) Prior Publication Data

US 2013/0211227 A1   Aug. 15, 2013

Related U.S. Application Data

(63) Continuation-in-part of application No. 12/508,559, filed on Jul. 23, 2009, now abandoned, which is a continuation-in-part of application No. 11/209,318, filed on Aug. 23, 2005, now Pat. No. 7,700,074, which is a continuation-in-part of application No. 11/117,126, filed on Apr. 27, 2005, now abandoned, which is a continuation-in-part of application No. 10/359,560, filed on Feb. 7, 2003, now abandoned.

(60) Provisional application No. 60/354,323, filed on Feb. 7, 2002.

(51) Int. Cl.

| | |
|---|---|
| *A61B 5/055* | (2006.01) |
| *A61K 49/00* | (2006.01) |
| *A61K 39/00* | (2006.01) |
| *A61K 39/38* | (2006.01) |
| *A61K 39/12* | (2006.01) |
| *A61K 39/21* | (2006.01) |
| *A61K 39/29* | (2006.01) |
| *A61B 5/00* | (2006.01) |
| *A61B 5/145* | (2006.01) |
| *A61K 31/22* | (2006.01) |

(52) U.S. Cl.
CPC ........... *A61B 5/0042* (2013.01); *A61B 5/14546* (2013.01); *A61B 5/4076* (2013.01); *A61K 31/22* (2013.01); *A61B 5/055* (2013.01); *A61B 5/4064* (2013.01)
USPC ........... 424/9.1; 424/9.2; 424/9.3; 424/181.1; 424/182.1; 424/183.1; 424/184.1; 424/185.1; 424/186.1; 424/187.1; 424/188.1; 424/189.1

(58) Field of Classification Search
CPC ............... A61B 5/0042; A61B 5/4076; A61B 5/14546; A61K 31/22
See application file for complete search history.

(56) References Cited

U.S. PATENT DOCUMENTS

| | | | | |
|---|---|---|---|---|
| 4,346,107 A | * | 8/1982 | Cavazza et al. | 514/547 |
| 5,208,037 A | * | 5/1993 | Wright et al. | 424/473 |
| 5,879,884 A | * | 3/1999 | Peroutka | 435/6 |
| 7,700,074 B2 | * | 4/2010 | Pettegrew et al. | 424/9.1 |

OTHER PUBLICATIONS

Pettegrew et al. (I), "31 P-MRS Study of Acetyl-L-Carnitine Treatment in Geriatric Depression: Preliminary Results," Bipolar Disorders, 4(1), 61-66 (Feb. 2002).*
Fulgente et al., "Laevo-Acetylcarnitine (Nicetile®) Treatment of Senile Depression," \Clinical Trials Journal, 27(3), 155-163 (1990).*
Casella et al., "L-Acetylcarnitine in Depressed Elderly Subjects. A Cross-Over Study vs. Placebo," Drugs Under Experimental and Clinical Research, 13(7), 417-423 (1987).*
Bella et al., "Effect of Acetyl-L-Carnitine on Geriatric Patients Suffering From Dysthymic Disorders," Int. J. Clinical Pharmacology Research, 10(6), 355-360 (1990).*
Pettegrew et al. (II), "Acetylk-L-Carnitine Physical-Chemical, Metabolic, and Therapeutic Properties: Relevance for its Mode of Action in Alzheimer's Disease and Geriatric Depression," Molecular Psychiatry, 5(6), 616-632 (2000).*
Garzya et al., "Evaluation of the Effects of L-Acetylcarnitine on Senile Patients Suffering from Depression," Drugs Under Experimental and Clinical Research, 16(2), 101-106 (1990).*
Alpha-GPC ((L-Alpha glycerylphosphorylcholine, Choline alfoscerate), on-line information published by Global Information Hub on Integrated Medicine, 2003: web address; <www.nhiondemand.com>.*
O'Neil et al. (eds.), The Merck Index, An Encyclopedia of Chemicals, Drugs and Biologicals, 13th Edition, 2001, Merck & Co., Whitehouse Station, NJ, only pp. 16 and 312 supplied, see entry entries 86 (acetylcarnitine) and 1862 (carnitine).*
Stanley et al., "Regionally Specific Alterations in Membrane Phospholipids in Children with ADHD: An In Vivo 31P Spectroscopy Study," Psychiatry Research, Neuroimaging, 148(2-3), 217-221 (2006).*
Keshavan et al., "Prefrontal Membrane Phspholipid Metabolism of Child and Adolescent Offspring at Risk for Schizophrenia or Schizoaffective Disorder: An In Vivo 31P MRS Study," Molecular Psychiatry, 8 (3), 316-323 (2003).*
Arias-Mendoza et al., "In Vivo Measurement of Phosphorus Markers of Disease," Disease Markers, 19(2-3), 49-68 (2003).*
Jensen et al., "Grey and White Matter Differences in Brain Energy Metabolism in First Episode Schizophrenia: 31P-MRS Chemical Shift Imaging at 4 Tesla," Psychiatry Research, Neuroimaging, 146(2), 127-135 (2006).*

\* cited by examiner

*Primary Examiner* — Lawrence E Crane
(74) *Attorney, Agent, or Firm* — Barbara E. Johnson, Esq.

(57) ABSTRACT

The invention is a method for the differential diagnosis of chronic schizophrenia or chronic alcoholism, by imaging the brain of a subject to detect any or all of the markers phosphocreatine (PCr), N-acetyl aspartate divided by the total creatine signal (NA/Cr$_t$), and synaptic phosphodiester (sPDE), and determining any increase or decrease in the presence of such markers compared to normal levels in specified anatomic areas of the brain. The output of such a method, resulting from such imaging, is presented to be viewed by a diagnostician in order to support the differential diagnosis based on the data output.

4 Claims, 13 Drawing Sheets

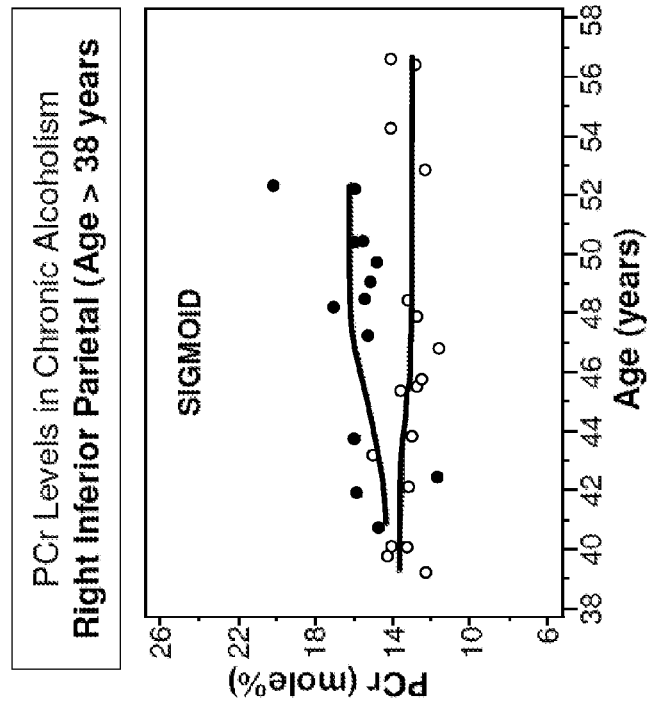
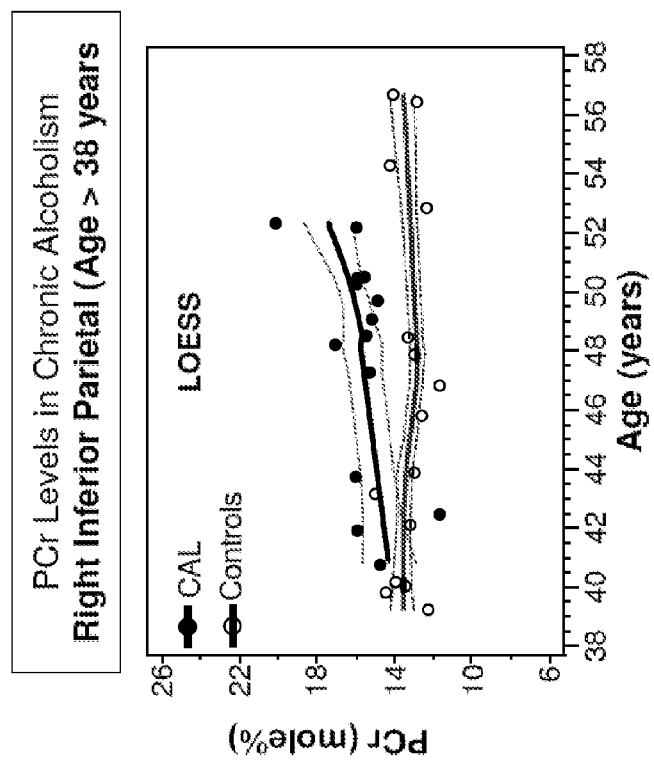
FIG. 5B
FIG. 5A

| PCr Marker | Inc. PCr, right prefrontal cortex, cognition intact | Inc. PCr, right inferior parietal, cognition intact | Inc. PCr, left superior temporal, cognition intact | Inc. PCr, right basal ganglia, cognition intact | Inc. PCr, right basal ganglia, cognition impaired | Inc. PCr, left prefrontal cortex, cognition impaired* | Inc. PCr, left basal ganglia, cognition impaired |
|---|---|---|---|---|---|---|---|
| Chronic Schizophrenia | X | | | | | X | X |
| Chronic Alcohol Syndrome | X | X | X | X | X | | |

*The average impairment rating scores (AIR) of chronic schizophrenia subjects significantly correlate with levels of PCr in left prefrontal cortex ($r = 0.34$, $p = 0.02$)

| sPDE Marker | Reduced sPDE, left basal ganglia, cognition intact | Reduced sPDE, Left Superior Temporal, Cognition intact | Reduced sPDE, Right Inferior Parietal, Cognition Impaired** | Reduced sPDE, Right Centrum Semiovale, Cognition impaired |
|---|---|---|---|---|
| Chronic Schizophrenia | | | | |
| Chronic Alcohol Syndrome | X | X | X | X |

**In chronic alcoholism subjects, sPDE levels in right inferior parietal region significantly correlate with Block Design scores ($r = 0.68$, $p=0.0011$)

| NA/Cr$_t$ Marker | Reduced NA/Cr$_t$, left superior temporal, cognition impaired | Reduced NA/Cr$_t$, Left basal ganglia cognition impaired | Reduced NA/Cr$_t$, Right occipital cortex cognition impaired | Reduced NA/Cr$_t$, left centrum semiovale, cognition impaired |
|---|---|---|---|---|
| Chronic Schizophrenia | X | | | |
| Chronic Alcohol Syndrome | | X | X | X |

FIG. 8

METHOD AND SYSTEM FOR DIFFERENTIAL DIAGNOSIS OF CHRONIC SCHIZOPHRENIA AND CHRONIC ALCOHOLISM

CROSS REFERENCE TO RELATED APPLICATIONS

This application is a continuation-in-part of U.S. patent application Ser. No. 12/508,559 filed 23 Jul. 2009, now abandoned, which is a continuation-in-part of U.S. patent application Ser. No. 11/209,318 filed 23 Aug. 2005, now U.S. Pat. No. 7,700,074, which was a continuation-in-part of U.S. patent application Ser. No. 11/117,126 filed 27 Apr. 2005, now abandoned, which was a continuation-in-part of U.S. Ser. No. 10/359,560 filed 7 Feb. 2003, now abandoned, which claimed priority to U.S. provisional patent application No. 60/354,323 filed 7 Feb. 2002, all of the above of which are hereby incorporated herein by reference.

BACKGROUND OF THE INVENTION

Field of the Invention

The present invention provides a biomarker diagnostic not only for chronic schizophrenia, but for the differential diagnosis of chronic schizophrenia and chronic alcoholism, regardless of the presence or absence of cognitive impairment.

SUMMARY OF THE INVENTION

Biomarker diagnosis of chronic schizophrenia in the presence of cognitive impairment is confirmed when phosphocreatine (PCr) levels are increased, compared to normal levels, in both the left and right prefrontal cortices of the brain, with increased PCr specifically also in the left basal ganglia and also reduced $NA/Cr_t$ in the left superior temporal region of the brain. $NA/Cr_t$ is N-acetyl aspartate (NA) divided by the total creatine signal $(Cr_t)$. By contrast, in a cognitively impaired individual a differential diagnosis of chronic alcoholism may be made when the patient exhibits increased PCr levels in the right basal ganglia, reduced $NA/Cr_t$ in all three of: the left basal ganglia; the right occipital cortex; and the left centrum semiovale, together with reduced synaptic phosphodiester "sPDE" (phosphodiester with short correlation time such as the breakdown products GPC and GPE produced from phosphatidylcholine and phosphatidylethanolamine respectively) signal in the right inferior parietal and the right centrum semiovale. In cognitively intact individuals, both the chronic schizophrenia patient and the chronic alcoholism patient will demonstrate increased PCr in the right prefrontal cortex, but unlike the chronic schizophrenia patient the cognitively intact chronic alcoholism patient also will exhibit increased PCr in the right inferior parietal, the left superior temporal, and the right basal ganglia, and will exhibit reduced sPDE in the left basal ganglia and in the left superior temporal region, whereas the chronic schizophrenia patient with intact cognition will comparatively present only with increased PCr in the right prefrontal cortex.

BRIEF DESCRIPTION OF THE DRAWINGS

FIG. 8 presents a table shows the attribution of various biomarkers increase or decrease quantification in various anatomic brain regions and the diagnostic attribution to chronic schizophrenia, chronic alcoholism, or both.

DETAILED DESCRIPTION OF THE INVENTION

Figure 1:
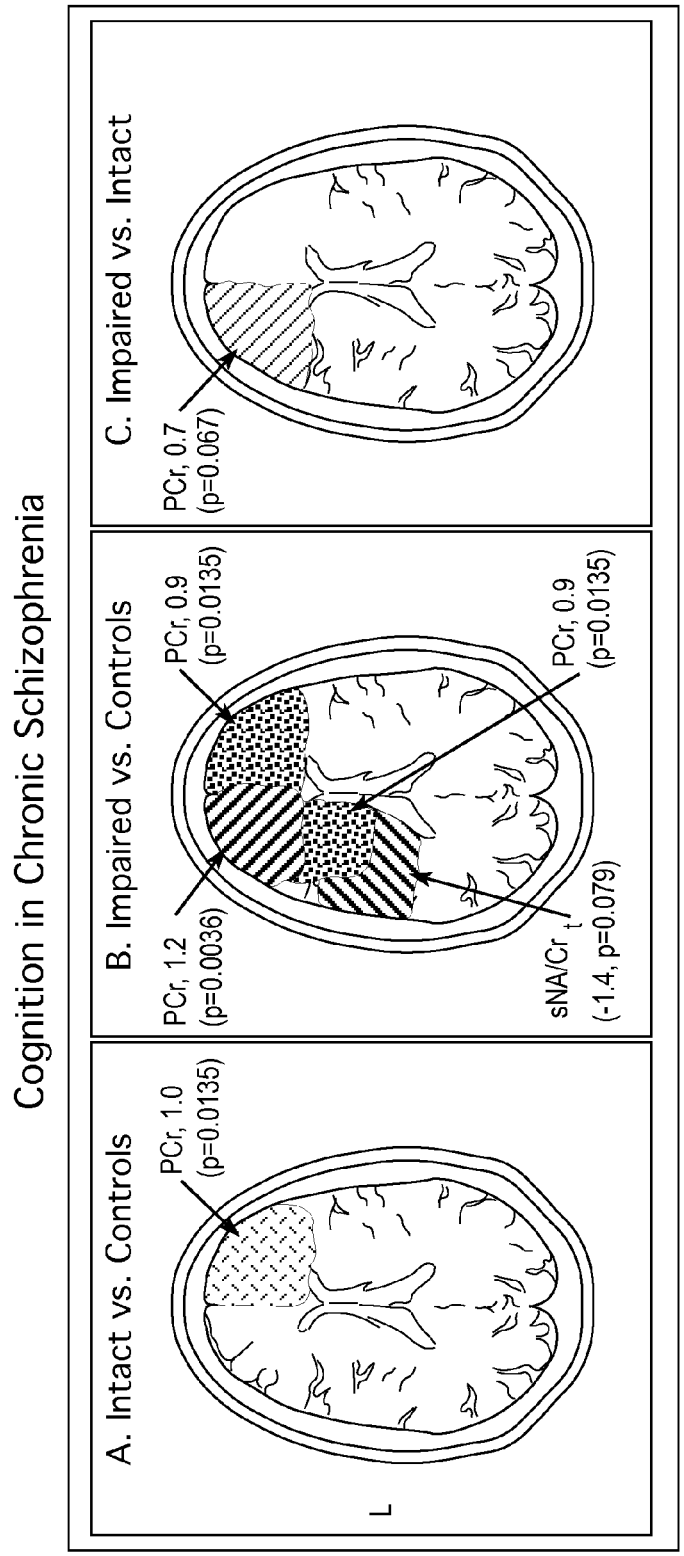
FIGS. 1A, B and C show Z-score plots distinguishing phosphocreatine (PCr), and N-acetyl aspartate (NA) divided by the total creatine signal $(Cr_t)$ or $NA/Cr_t$ biomarkers in cognitive intact chronic schizophrenia brains versus controls, cognitive impaired chronic schizophrenia brains versus controls, and cognitively impaired versus intact chronic schizophrenia brains.

Biomarker diagnosis of chronic schizophrenia in the presence of cognitive impairment is confirmed when phosphocreatine (PCr) levels are increased, compared to normal levels, in both the left and right prefrontal cortices of the brain, with increased PCr specifically also in the left basal ganglia and also reduced $NA/Cr_t$ in the left superior temporal region of the brain. $NA/Cr_t$ is N-acetyl aspartate (NA) divided by the total creatine signal $(Cr_t)$. By contrast, in a cognitively impaired individual a differential diagnosis of chronic alcoholism may be made when the patient exhibits increased PCr levels in the right basal ganglia, reduced $NA/Cr_t$ in all three of: the left basal ganglia; the right occipital cortex; and the left centrum semiovale, together with reduced synaptic phosphodiester sPDE (phosphodiesters with short correlation time such as the breakdown products of GPC and GPE produced from phosphatidylcholine and phosphatidylethanolomine respectively) signal in the right inferior parietal and the right centrum semiovale. In cognitively intact individuals, both the chronic schizophrenia patient and the chronic alcoholism patient will demonstrate increased PCr in the right prefrontal cortex, but unlike the chronic schizophrenia patient the cognitively intact chronic alcoholism patient also will exhibit increased PCr in the right inferior parietal, the left superior temporal region, and the right basal ganglia, and will exhibit reduced sPDE in the left basal ganglia and in the left superior temporal region, whereas the chronic schizophrenia patient with intact cognition will comparatively present with increased PCr only in the right prefrontal cortex.

The PCr, $NA/Cr_t$, and sPDE biomarkers themselves, as well as techniques to assay their presence and quantity in the human brain, are already known from my previous published and patented work, such as U.S. Pat. No. 7,700,074. In U.S. Pat. No. 7,700,074 (incorporated herein by reference without limitation) I have described how to quantify PCr, N-acetyl aspartate and (s)PDE with medical imaging techniques, such as Z-score plots using dichotomized data summarizing regional phosphorus-hydrogen magnetic resonance spectroscopic imaging ($^{31}P$—$^{1}H$ MRSI)— differences known in the art. The novel feature of the present invention is assessing the increase or decrease of particular biomarkers in very specific anatomic regions in the brain, where these various markers are reduced or increased and the differential diagnostic significance thereof. How to image the markers themselves, throughout the brain, is already known from my previous published and patented work.

Referring now to FIG. 8, it is easiest to envision the differential diagnosis possible with the instant invention when viewing the comparative loci of marker increase or decrease and the attribution to chronic schizophrenia or chronic alcoholism. As FIG. 8 shows, increase in PCr level occurs in the right prefrontal cortex for both chronic schizophrenia and chronic alcoholism if the patient does not have cognitive impairment regardless of whether the patient has chronic schizophrenia or chronic alcoholism (or both). However, as to all the other markers shown in FIG. 8, the marker, its increase or decrease, and anatomic location in the brain, is specific to either chronic schizophrenia or chronic alcoholism, without overlap. Therefore, at a minimum at least one of the biomarkers for either chronic schizophrenia or chronic alcoholism as shown in FIG. 8 has diagnostic significance for chronic schizophrenia or chronic alcoholism, and ideally a patient will be assessed for all the applicable markers and anatomic locations described in FIG. 8 in order to permit differential diagnosis of chronic schizophrenia or chronic alcoholism from the results of the biomarker tests. In its most complete iteration, therefore, the present invention allows differential diagnosis of chronic schizophrenia in the presence of cognitive impairment when not only the right prefrontal cortex shows increased PCr but also the left prefrontal cortex shows increased PCr also, the left basal ganglion shows increased PCr, and the left superior temporal exhibits reduced $NA/Cr_t$. Likewise, in a cognitively impaired individual a differential diagnosis of chronic alcoholism may be made when the patient exhibits increased PCr in the right basal ganglia, reduced $NA/Cr_t$ in all three of: the left basal ganglia; the right occipital cortex; and the left centrum semiovale, together with reduced sPDE signal in both the right inferior parietal and the right centrum semiovale. Finally, as described above, in cognitively unimpaired individuals, both the chronic schizophrenia patient and the chronic alcoholism patient will demonstrate increased PCr in the right prefrontal cortex, but unlike the chronic schizophrenia patient the cognitively intact chronic alcohol patient also will exhibit increased PCr in the right inferior parietal, the left superior temporal region, and the right basal ganglia, and will exhibit reduced sPDE in the left basal ganglia and in the left superior temporal region, whereas the chronic schizophrenia patient with intact cognition will comparatively present with increased PCr only in the right prefrontal cortex. If a patient exhibits all the markers shown in FIG. 8, the presence of both chronic schizophrenia and chronic alcoholism may be confirmed.

The remainder of this patent specification describes the research on which the above conclusions are based, and provides additional description of the Figures included herewith.

LOESS and sigmoidal curve fitting of brain molecular data obtained by $^{31}P$—$^{1}H$ MRSI was used to examine age-related changes in brain regional metabolite levels in cohorts of chronic schizophrenia, chronic alcoholism and match control subjects as well as chronic smokers. The chronic smokers allowed examination of the possible confound of smoking since both chronic schizophrenia and chronic alcoholism subjects are usually heavy smokers. The chronic schizophrenia and chronic alcoholism cohorts were dichotomized into cognitive intact or impaired subgroups. The metabolites measured were phosphocreatine (PCr), phosphomonoesters with short correlation times (sPME) which are precursors of membrane phospholipids and phosphodiesters with short correlation times (sPDE) which are membrane phospholipid breakdown products. In addition, we measured N-acetyl-containing molecules which in brain are predominantly N-acetyl aspartate, generally expressed as NA divided by the total creatine signal $Cr_t$, or $NA/Cr_t$. NAA (N-acetyl aspartate itself) is thought to be a marker of neurons and neuronal processes. Chronic alcoholism was chosen as a comparison group for chronic schizophrenia due to similar cognitive deficits, but some cognitive differences also are observed. Because the cognitive abnormalities of the two disorders share similarities and differences, our research investigated whether there are also similarities and differences in brain molecular abnormalities, and ultimately led to the conclusions summarized in FIG. 8 herewith.

Figure 2:
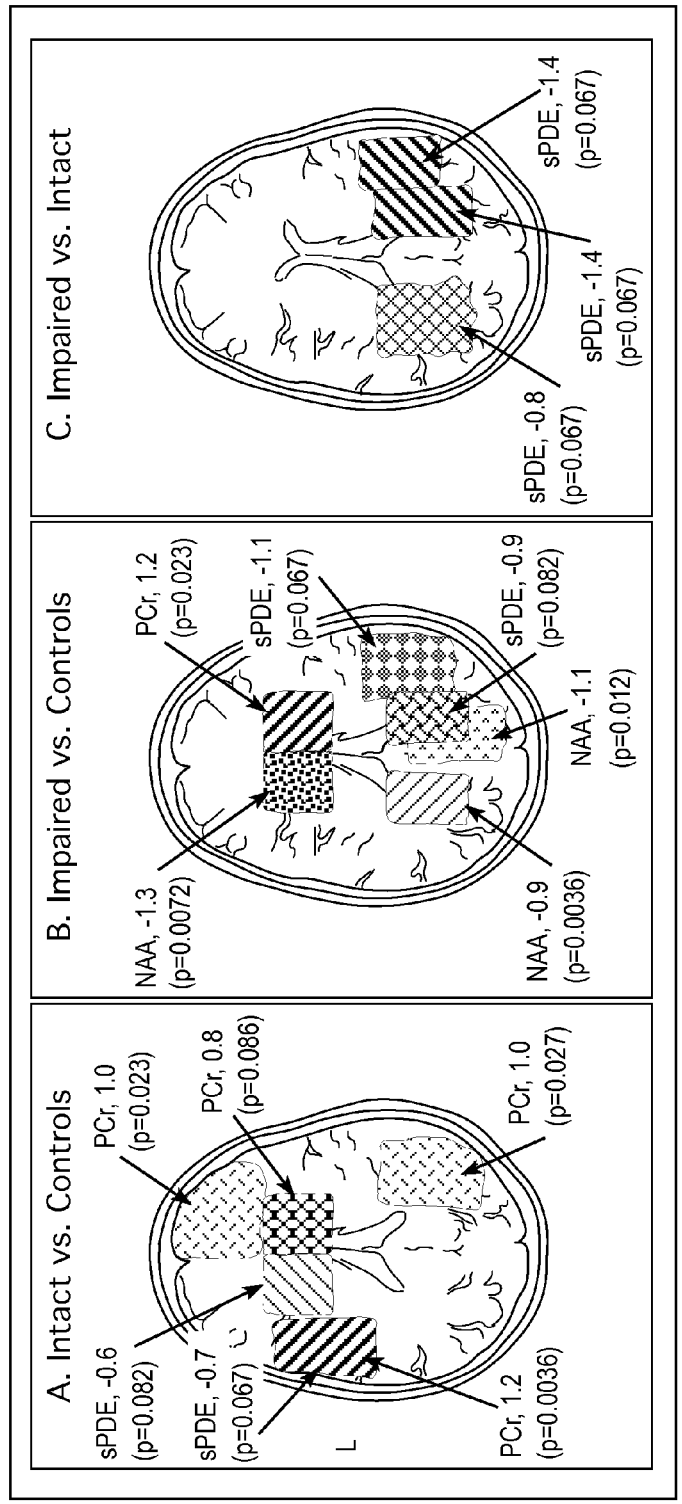
FIGS. 2A, B and C show Z-score plots distinguishing phosphocreatine (PCr), N-acetyl aspartate itself (NAA), and synaptic phosphodiester (sPDE) markers in cognitively intact chronic alcoholism brains versus controls, cognitively impaired chronic alcoholism brains versus controls, and cognitively impaired versus cognitively intact chronic alcoholism.
Figure 3B:
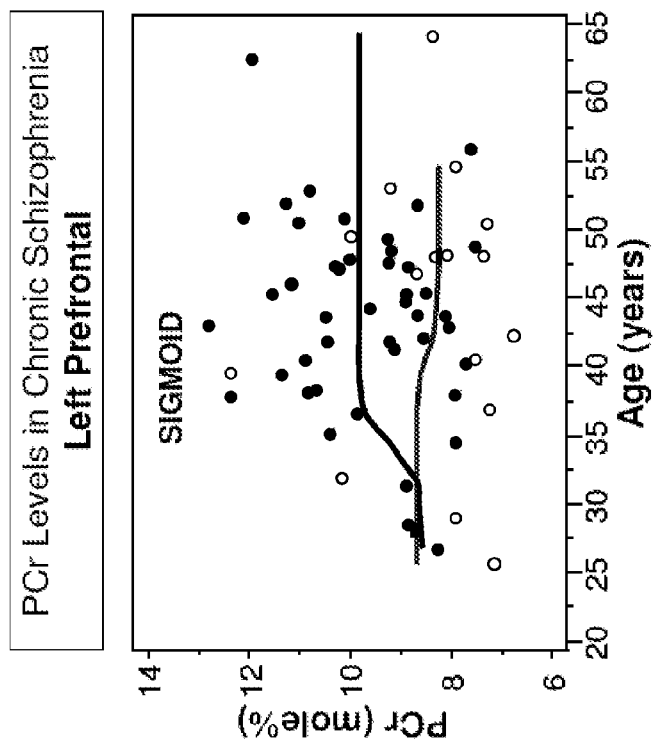
FIGS. 3A, B, C and D are line graphs showing PCr markers in the left prefrontal cortex in chronic schizophrenia.
Figure 3A:
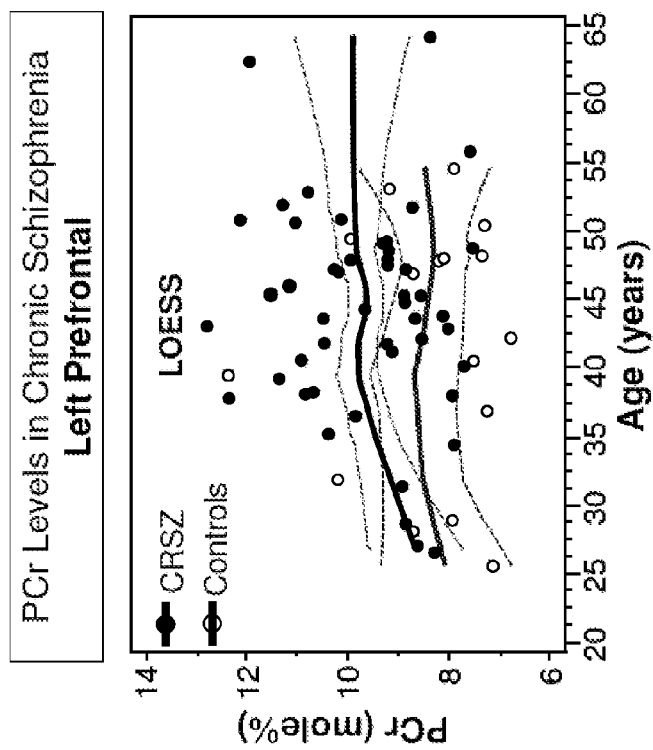
Figure 3D:
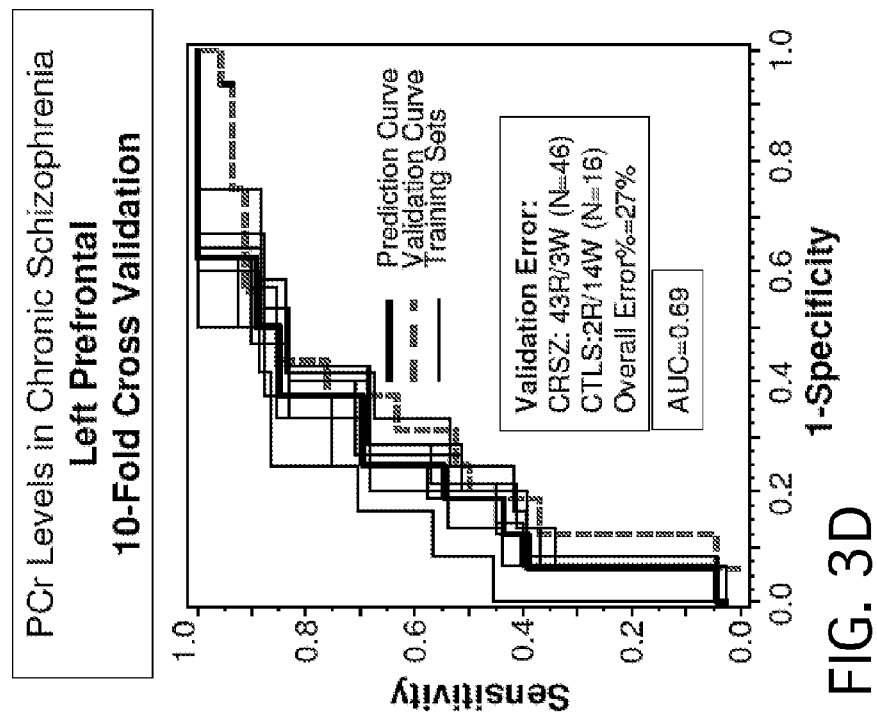
Figure 3C:
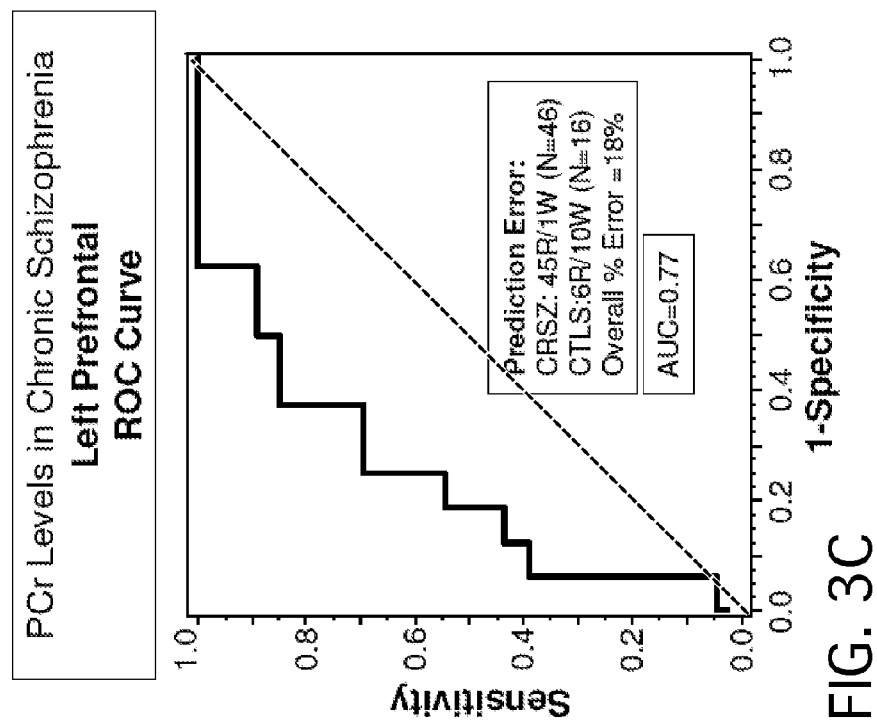
Figure 4B:
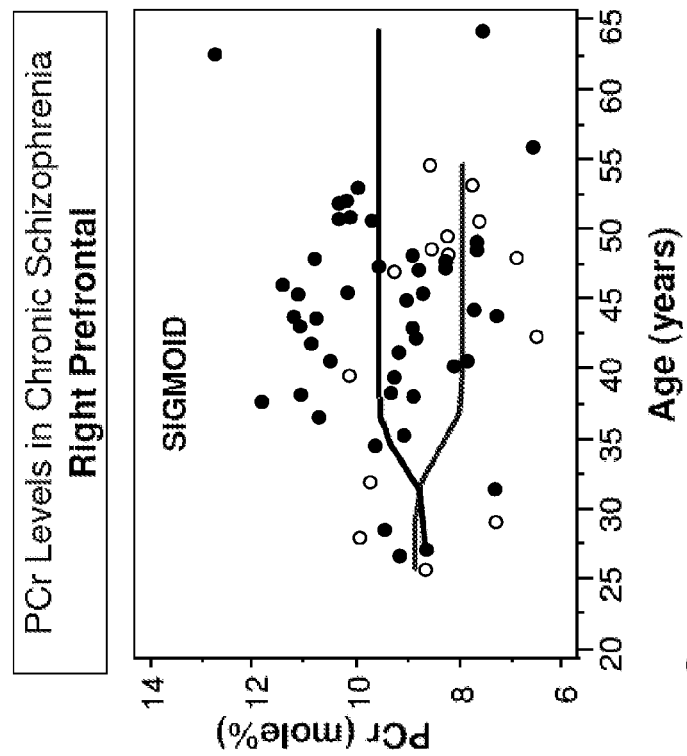
FIGS. 4A, B, C and D are line graphs showing PCr markers in the right prefrontal cortex in chronic schizophrenia.
Figure 4A:
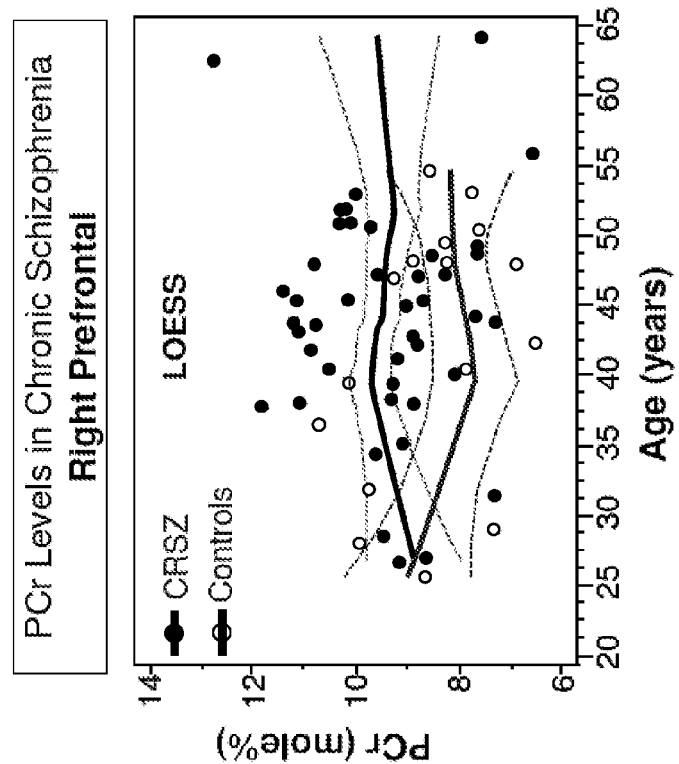
Figure 4D:
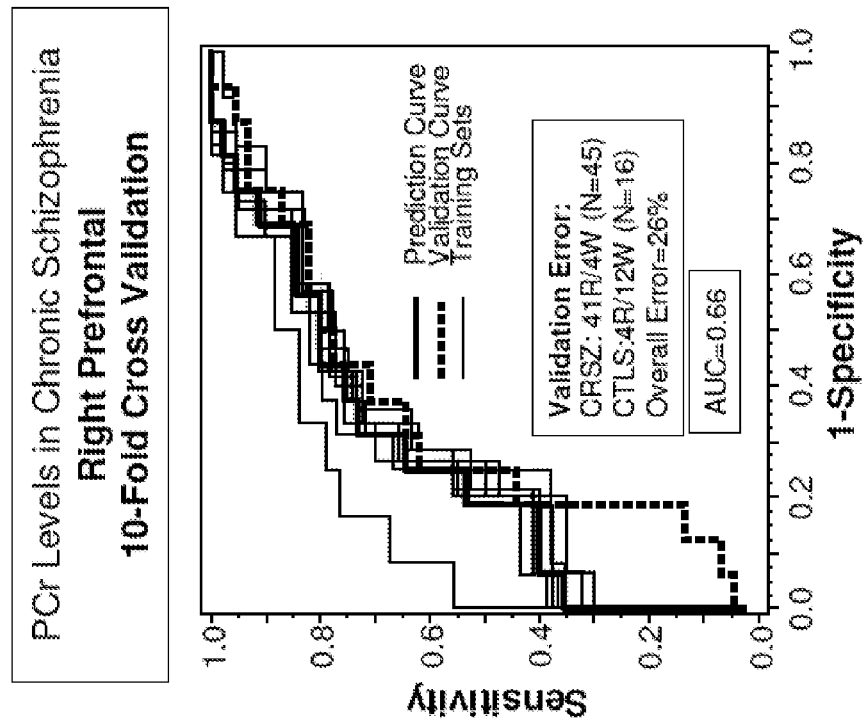
Figure 4C:
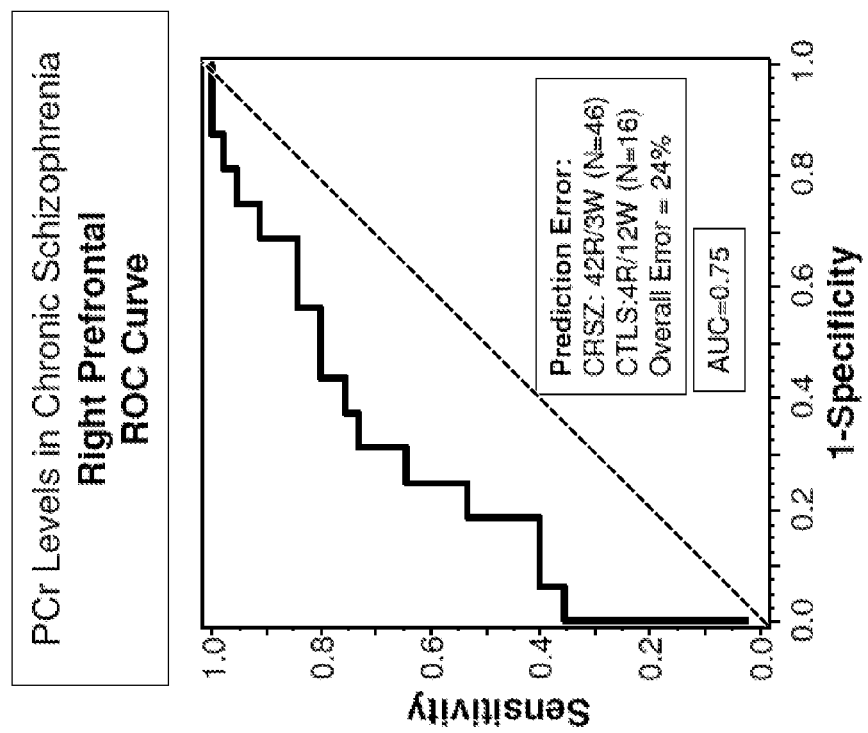
Figure 5D:
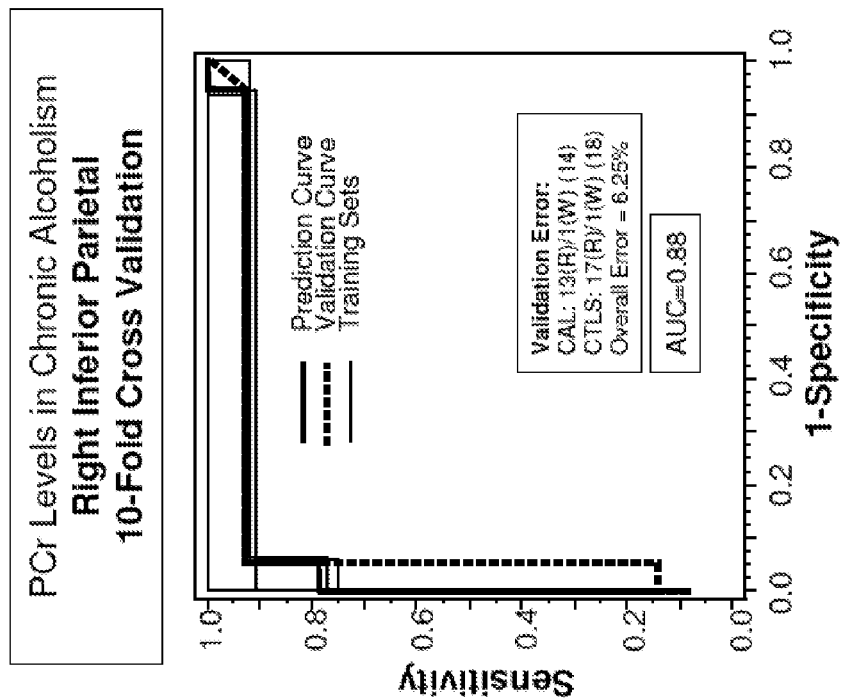
FIGS. 5A, B, C and D are line graphs showing PCr markers in the right inferior parietal cortex in chronic alcoholism.
Figure 5C:
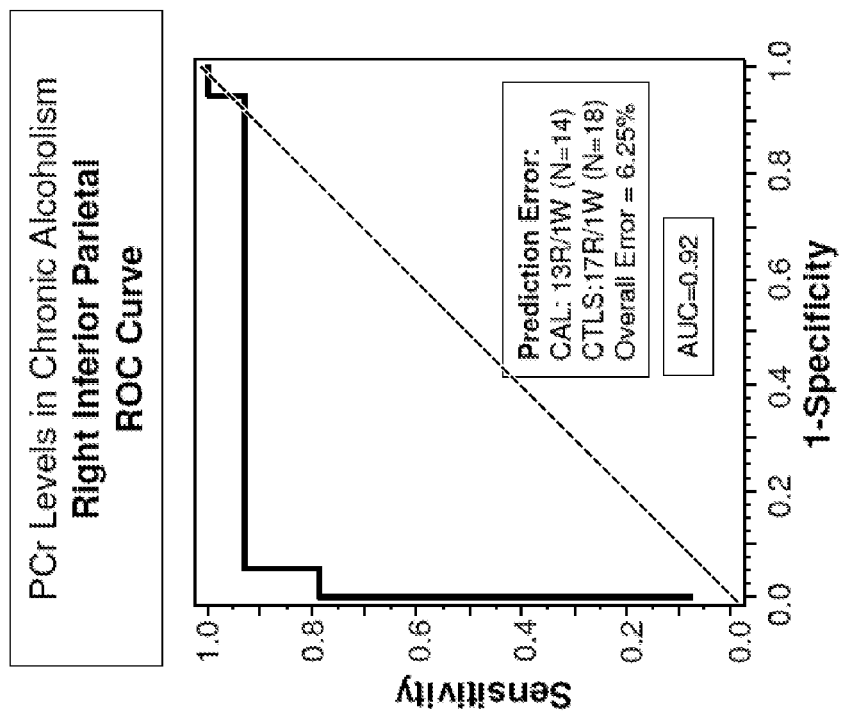
Figure 6B:
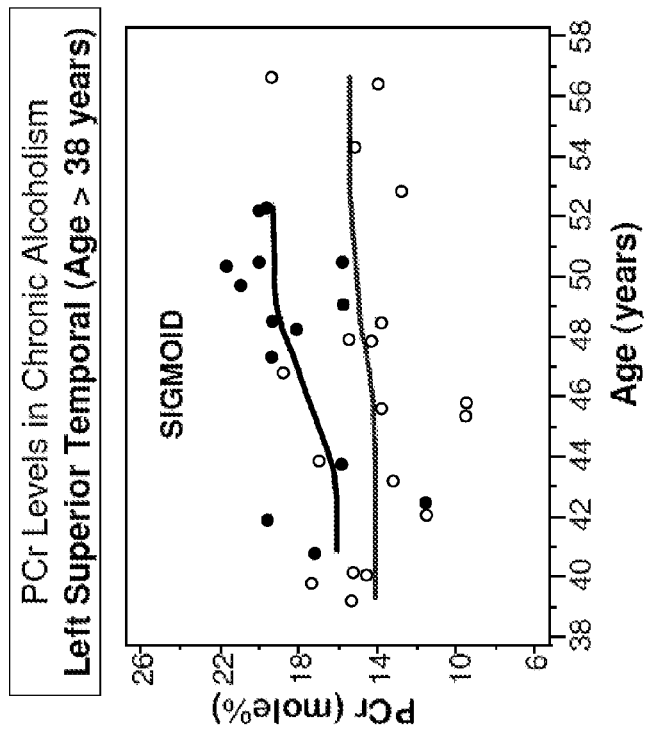
FIGS. 6A, B, C and D are line graphs showing PCr markers in the left superior temporal region in chronic alcoholism.
Figure 6A:
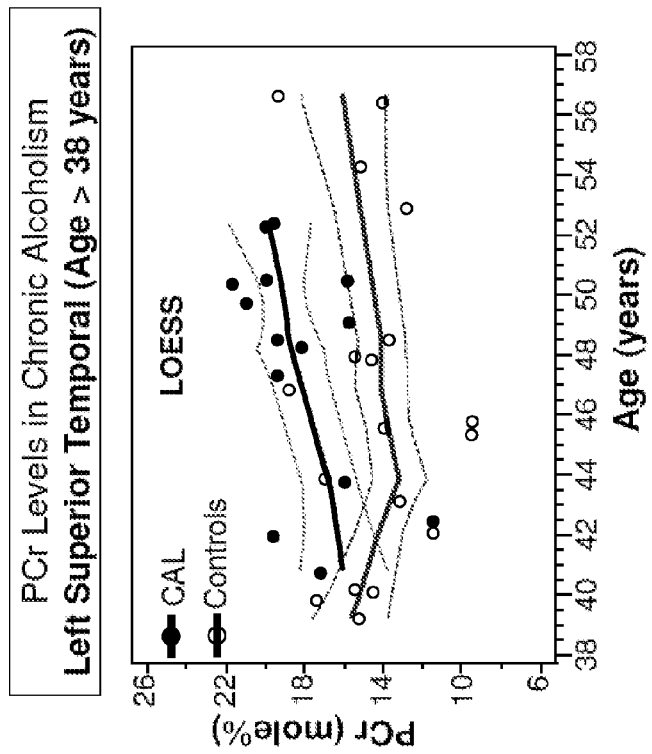
Figure 6D:
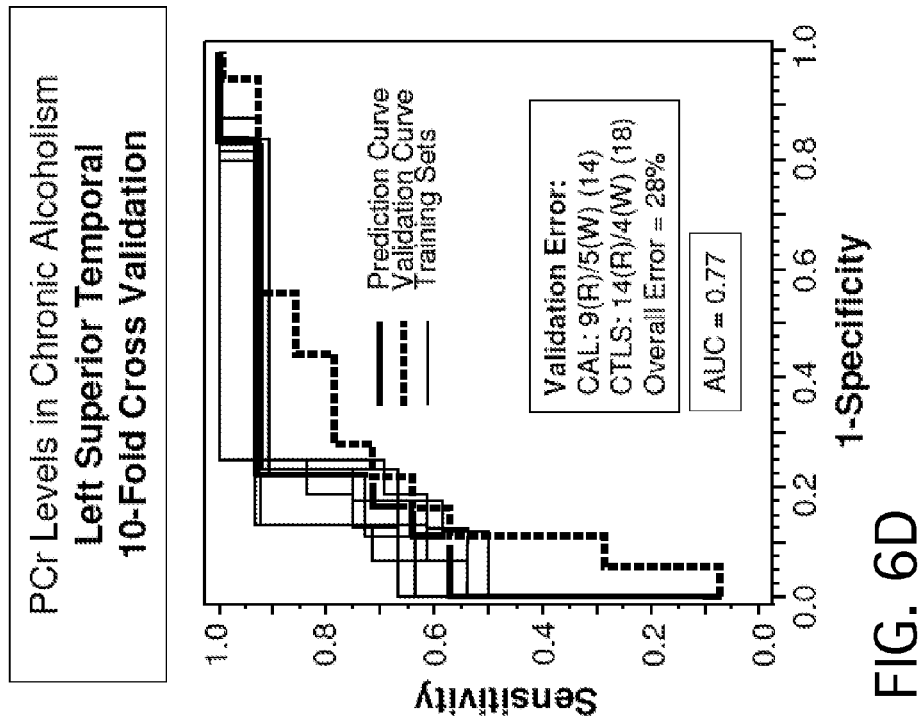
Figure 6C:
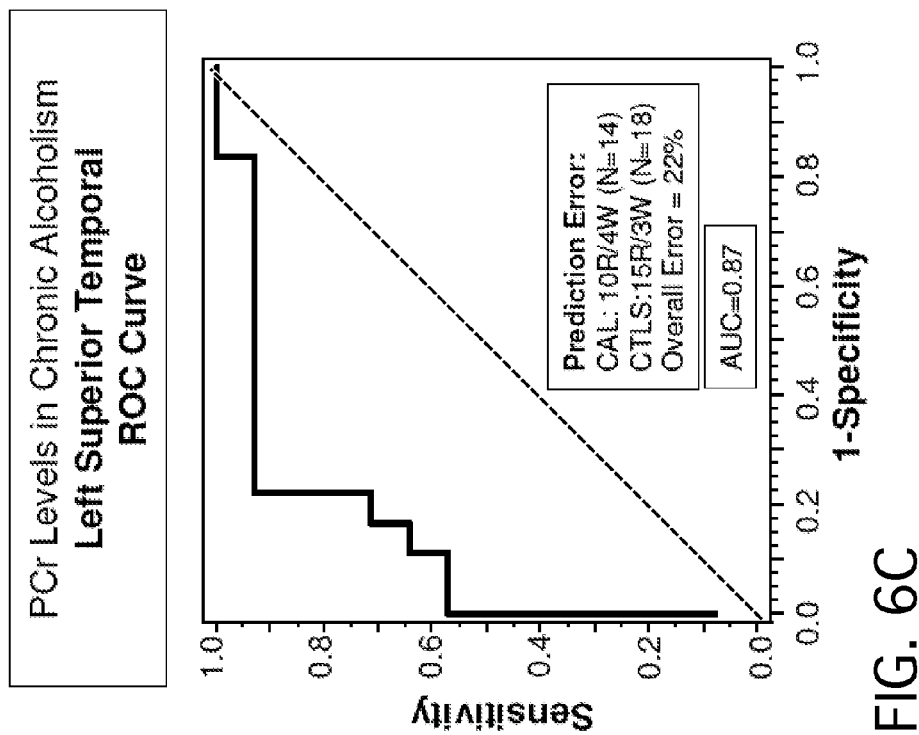
Figure 7B:
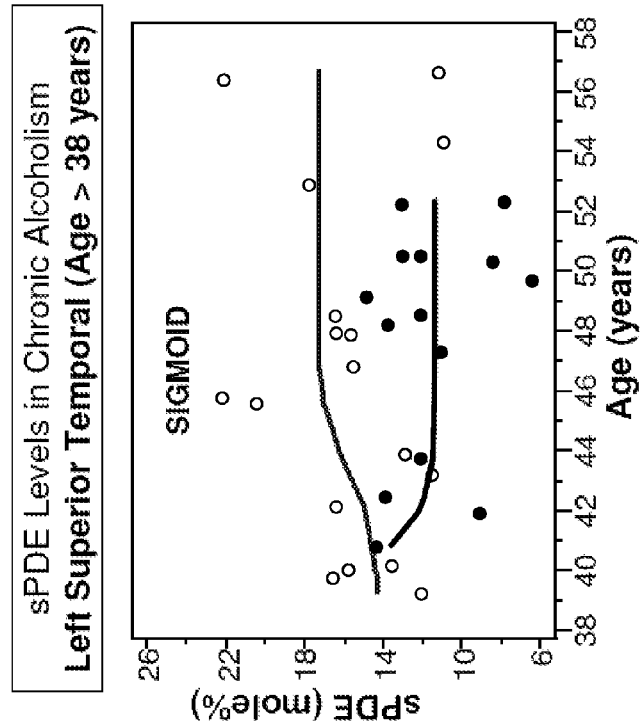
FIGS. 7A, B, C and D are line graphs showing sPDE markers in the left superior temporal region in chronic alcoholism.
Figure 7A:
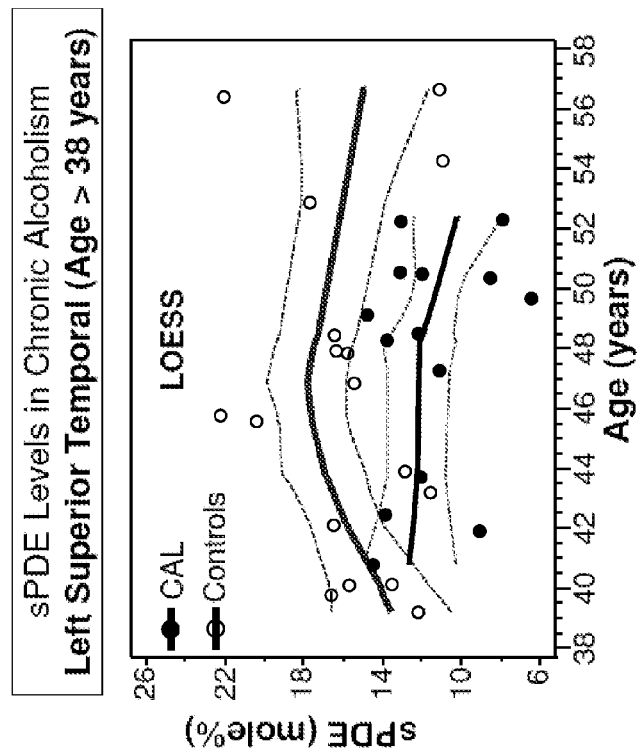
Figure 7D:
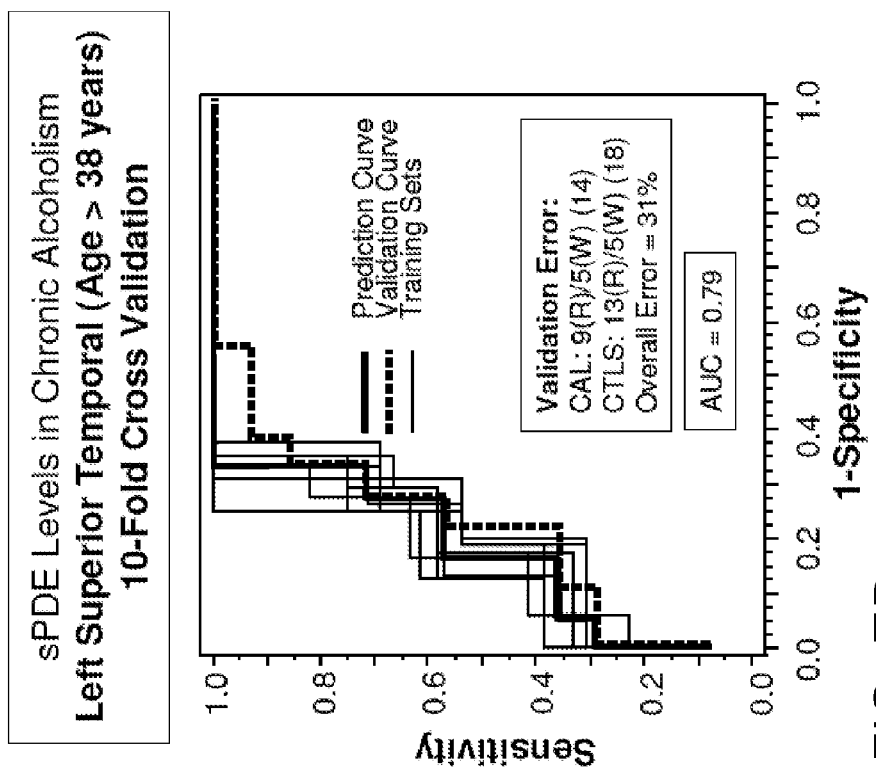
Figure 7C:
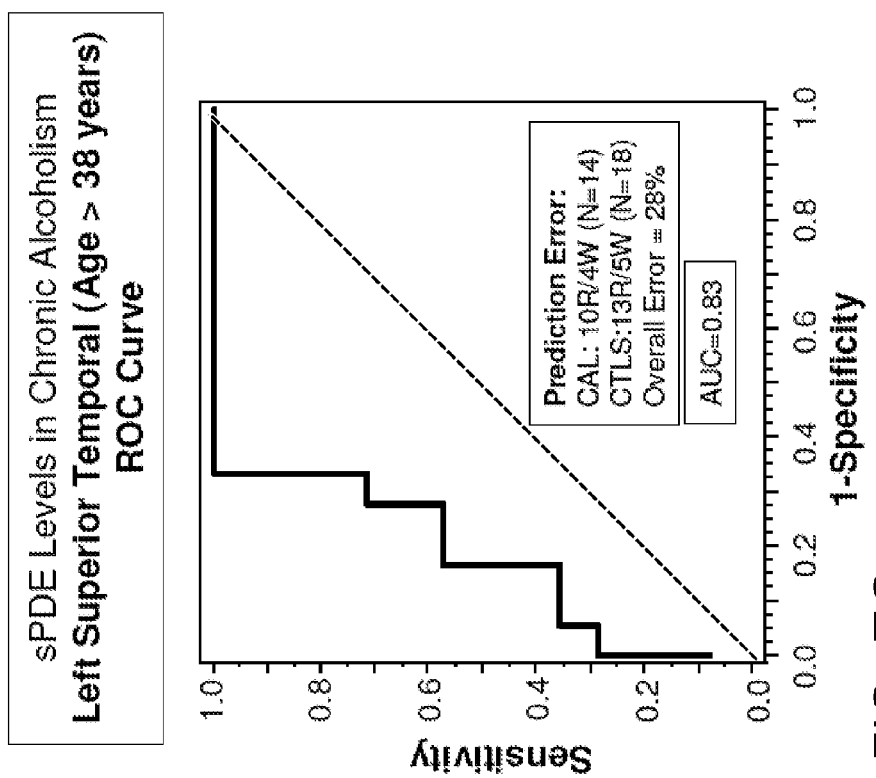

The increased level of PCr in the prefrontal cortex of chronic schizophrenia subjects reflects reduced synaptic terminals with reduced utilization of PCr. The prefrontal cortex undergoes synaptic elimination in humans during late-adolescence to young-adult life, which is the same time frame as the usual onset of clinical symptoms in chronic schizophrenia. In view of the data represented in FIGS. 1-7 and the application of those results as summarized in FIG. 8, we have investigated and validated the anatomic regions for particular biomarker and biomarker combinations to provide differential diagnosis of chronic schizophrenia and chronic alcoholism with or without cognitive impairment.

Although the invention has been described with particularity above, the invention is only to be considered to be limited insofar as is set forth in the accompanying claims.

The invention claimed is:

1. A method for the differential diagnosis of chronic schizophrenia or chronic alcoholism, comprising imaging the brain of a subject in need of diagnosis for the markers phosphocreatine (PCr), N-acetyl aspartate divided by the total creatine signal ($NA/Cr_t$), and synaptic phosphodiester (sPDE) and determining any increase or decrease in the presence of said markers compared to normal levels in specified anatomic areas of the brain, and outputting the results of the imaging as one or more files or images to be viewed by a diagnostician.

2. The method according to claim 1, wherein after quantifying PCr, $NA/Cr_t$ and sPDE, a determination that (1) PCr levels are increased, compared to normal levels, in both the left and right prefrontal cortices of the brain, together with (2) increased PCr specifically also in the left basal ganglia and also (3) reduced $NA/Cr_t$ in the left superior temporal region of the brain, all taken together confirm a differential diagnosis of chronic schizophrenia when cognitive impairment is present.

3. The method according to claim 1, wherein after quantifying PCr, $NA/Cr_t$ and sPDE, a determination that (1) phosphocreatine (PCr) levels are increased in the right basal ganglia, with (2) reduced $NA/Cr_t$ in all three of: (a) the left basal ganglia; (b) the right occipital cortex; and (c) the left centrum semiovale, together with (3) reduced sPDE in the right inferior parietal and the right centrum semiovale, taken together confirm a differential diagnosis of chronic alcoholism when cognitive impairment is present.

4. The method according to claim 1, wherein after quantifying PCr, $NA/Cr_t$ and sPDE, in cognitively intact individuals the profile wherein (1) increased PCr in the right prefrontal cortex plus (2) increased PCr in (a) the right inferior parietal, (b) the left superior temporal region, and (c) the right basal ganglia, and (3) reduced sPDE in (a) the left basal ganglia and (b) in the left superior temporal region, taken together confirm a differential diagnosis of chronic alcoholism in place of a diagnosis of chronic schizophrenia.

* * * * *